United States Patent [19]
Macovski

[11] Patent Number: 4,686,695
[45] Date of Patent: Aug. 11, 1987

[54] SCANNED X-RAY SELECTIVE IMAGING SYSTEM

[75] Inventor: Albert Macovski, Menlo Park, Calif.

[73] Assignee: Board of Trustees of the Leland Stanford Junior University, Stanford, Calif.

[21] Appl. No.: 207,351

[22] Filed: Nov. 17, 1980

Related U.S. Application Data

[63] Continuation of Ser. No. 9,484, Feb. 5, 1979, abandoned.

[51] Int. Cl.⁴ ............................................. G03B 41/16
[52] U.S. Cl. .................................... 378/146; 378/5; 378/99
[58] Field of Search .................... 378/5, 19, 146, 99, 378/100, 111

[56] References Cited

U.S. PATENT DOCUMENTS

| | | | |
|---|---|---|---|
| 2,730,566 | 1/1956 | Bartow | 378/100 |
| 3,101,407 | 8/1963 | Shipman | 378/146 |
| 3,633,029 | 1/1972 | Duffy | 378/106 |
| 3,848,130 | 11/1974 | Macovski | 378/5 |
| 3,866,047 | 2/1975 | Hounsfield | 378/14 |
| 4,029,963 | 6/1977 | Alvarez | 378/5 |
| 4,096,391 | 6/1978 | Barnes | 378/146 |
| 4,196,352 | 4/1980 | Berninger | 378/9 |
| 4,247,774 | 1/1981 | Brooks | 378/5 |
| 4,260,898 | 4/1981 | Annis | 378/146 |

OTHER PUBLICATIONS

"Radiological Contrast Enhancing Methods", Jacobson et al., *Advances in Biological and Medical Physics*, Academic Press, date unknown, pp. 201-260.
X-Ray Spectrophotometry in Vivo", Jacobson, American Journal of Roentgenology, vol. 91, 1/64, pp. 202-210.

*Primary Examiner*—Craig E. Church
*Attorney, Agent, or Firm*—Flehr, Hohbach, Test, Albritton & Herbert

[57] ABSTRACT

An x-ray beam is scanned through a sequence of subsections of a volume. At each position the x-ray transmission is measured at two energies. The resultant transmission signals are processed to produce a signal representing the projected amount of a specific material in the volume. The two energies are chosen so that the mass attenuation coefficients of bone and soft tissue are comparable to each other.

41 Claims, 10 Drawing Figures

SCANNED X-RAY SELECTIVE IMAGING SYSTEM

This is a continuation of application Ser. No. 009,484 filed Feb. 5, 1979, now abandoned.

BACKGROUND OF THE INVENTION

1. Field of the Invention

This invention relates to x-ray projection imaging systems. In a primary application the invention relates to obtaining projection x-ray images of a specific material in a volume of the body. In another application the invention relates to obtaining isolated images of blood vessels without bone and soft tissue using non-invasive injections of iodinated contrast material.

2. Description of Prior Art

At present images of blood vessels are made using invasive procedures where a catheter is inserted into the vessel and large amounts of an iodinated contrast material is inserted. The large amount is necessary to sufficiently attenuate x-rays so that the vessels will be visible. There have been a number of efforts to provide greater sensitivity to the iodine so that the vessels can be imaged with a non-invasive injection of iodine into a peripheral vein. Thusfar these have been relatively unsuccessful. In general much of the efforts at obtaining improved sensitivity to iodinated contrast agents concentrated on utilizing the unique energy spectral characteristics of iodine compared to those of body tissues.

The earliest approaches used relatively slow techniques which required long exposure times. These long exposure times are inadequate for imaging vessels which exhibit significant motion, as many do. Some of these early approaches used low-power monoenergetic sources on either side of the K edge of iodine. A system of this type using mechanically scanned x-ray beams and mechanical analog computers is described in Vol. VI of the *Advances in Biological and Medical Physics* published by the Academic Press in the chapter by B. Jacobson and R. Stuart Mackay on "Radiological Contrast Enhancement Methods." The section labelled "Dichromography," from page 224 to 231 describes a system using a special x-ray source with two fluorescent secondary emitters which alternately generated two monochromatic x-ray beams having energies on either side of the iodine K absorption edge. At each point wedge shaped materials of known composition are translated across the beam until the output beam reaches its predetermined value. The thickness of the wedges is then a direct indication of the amounts of the particular material present. A similar approach is described by B. Jacobson in the *American Journal of Roentgenology*, Vol. 91, January 1964, entitled "X-ray Spectrophometry in Vivo." In this paper a similar secondary emissive source alternately produced three monoenergetic wavelengths. Wedges of a soft tissue equivalent, bone and iodine were used in a mechanical analog computer to determine the amount of these body materials at each point in the scan.

Although these systems gave interesting results they suffered from using low power sources which required a long time to create an image. Normal heart and respiratory motions during the scanning time resulted in a blurred, low-resolution image. The low power of the sources was due to the use of monoenergetic beams.

At present, sufficient x-ray power for rapid exposures can only be derived from x-ray tubes. There is an early brief reference to the use of x-ray tube sources in an energy selective system in Appendix II of "Television X-ray Movies: Dose and Contrast Factors" by R. S. Mackay in the *IRE Transactions on Medical Electronics*, Vol. ME-7, No. 2, Apr. 1960, pp. 80–86. In this paper a heterochromatic source is used to produce different x-ray wavelengths. The various transmitted energies are detected using a scintillation detector and pulse height analyzer. A scanning beam is used, thus analyzing the tissue one point at a time. Since pulse height analyzers must isolate single photon events, this system is very slow. The long scan time makes it impractical for radiographic studies.

A number of studies have been made of isolating the iodinated contrast material by filtering an x-ray tube source on either side of the K edge of iodine. One such system is described in U.S. Pat. No. 3,854,049 issued to Charles A. Mistretta. In this system the x-ray beam is alternately filtered by a rotating filter wheel. Each filter produces a relatively narrow spectrum on either side of the K absorption edge of iodine. The television fluoroscopic images resulting from each filter are subtracted to provide an isolated image of the iodine.

These systems have thusfar been unable to provide non-invasive images of small vessels such as the coronary arteries for a number of reasons. Imaging detectors such as television-fluoroscopic systems or screen-film systems contain significant amounts of additive noise over and above the fundamental quantum noise due to the captured x-ray photons. These additive noise components obscure the detection of small difference signals as would be encountered with small vessels. Also, heavily filtered quasi-monoenergetic beams are relatively low in power, thus reducing the desired signal intensity. In addition, x-ray energies in the vicinity of the iodine K edge of 33 kev have relatively low transmission through the body since the attenuation coefficient of tissue is relatively high in this region. This further reduces the intensity of the desired signals as compared to the noise.

In general, imaging detectors, which simultaneously acquire the entire x-ray image, have a number of serious problems in systems attempting to isolate small amounts of iodine. As previously indicated, they have additive noise problems. Also, these systems are subject to significant amounts of scattered radiation since the entire volume is being irradiated simultaneously. Each imaging point thus receives scattered radiation from the entire volume. This scatter is reduced by the scatter-reducing grids, but it remains a significant noise source. In addition, imaging detectors are faced with fundamental tradeoffs between resolution and capture efficiency. If thick screens are used the capture efficiency of photons will be high, but the increased spreading of the light results in poor resolution. Conversely, thin screens produce high resolution and low capture efficiency. It is for these reasons that the present invention utilizes non-imaging detectors where a subsection of the image is acquired at each time.

The use of filtered spectra on either side of the K edge results in some error because of the finite width of the energy spectrum. These errors are particularly large in the case of bone whose attenuation coefficient varies significantly in this region. These systems can be compensated for by the use of a third energy as described in a publication by F. Kelcz, C. A. Mistretta and S. J. Riederer, "Spectral Considerations for Absorption Edge Fluoroscopy" in *Medical Physics*, Vol. 4, pp. 26–35, 1977. The output from this third energy can compensate for the bone errors, but the other problems, such as those due to the use of imaging detectors, remain.

A generalized system providing isolated images of specific materials is described in U.S. Pat. No. 3,848,130 issued to Albert Macovski. In this system transmission measurements are made at various energies and processed to provide isolated material images. Methods are shown for processing signals obtained from broad energy spectra so that narrow band filtering is not required. However, this system uses imaging detectors, including television fluoroscopy and film, so that the previously described problems will prevent the non-invasive visualization of small vessels.

In general all of the systems in the prior art used relatively low energies for the isolation of iodine in an attempt to take advantage of the large changes in the iodine attenuation coefficient. However, these lower energies present significant problems as was previously mentioned. The relatively low transmission of the body reduces the detected signals and increases the quantum noise. Also, at these lower energies, the mass attenuation coefficient of bone and soft tissue are quite different. This difference makes it difficult to provide an isolated iodine image in the presence of both soft tissue and bone.

In general, in the diagnostic region of the energy spectrum, the attenuation coefficients of all materials can be decomposed into a photo-electric component and a Compton scattering component. In U.S. Pat. No. 4,029,963 issued to R. E. Alvarez and A. Macovski, measurements are made at two energies spectra with the resultant signals processed to produce images of the photoelectric and Compton-scattering components. This system is used for both single projection images and for cross-sectional images using computerized tomography. In the single projection images, however, imaging detectors are used with all of the attendant problems of limited performance previously described. This patent also describes the concept of energy-sensitive integrating detectors. A dual detector is shown which simultaneously provides separate measurements at high and low energy spectra.

To obtain the desired accuracy it is important to obtain efficient, low-noise x-ray measurements which are essentially free of scatter. These are presently obtained in all of the commercial systems of computerized tomography. The scatter is not a problem since a relatively small region is irradiated at any one time using either a pencil beam or a sheet beam. The attendant collimation at the detector all but eliminates the scatter. The detectors used are individual high-efficiency detectors arranged in arrays. The thickness of the detectors determines the efficiency and the lateral dimensions determines the resolution. These are relatively independent since the detectors are isolated and provide separate measurements. Most important, the detectors are essentially free of additive noise. The relatively large electrical signals produced by either photo-multipliers or Xenon detectors are limited solely by quantum noise so that the accuracy is determined solely by the amount of radiation.

These accurate detectors are beginning to be used for single projection radiography. In the Microdose system produced by American Science and Engineering and in the Scout View System produced by General Electric the computerized tomography instrument is modified to provide a projection image. The body is indexed through the fan beam with the detector array providing a sequence of line information to produce a transmission image. Initially these transmission images were designed to identify the anatomy so as to facilitate the choice of the desired level for the cross-sectional image. Because of the detection accuracy, however, they have provided high-quality transmission images which have diagnostic value in their own right. These images, however, are not capable of non-invasive visualization of small vessels because of the intervening tissue. These are single energy spectra systems which are not capable of obtaining isolated images of specific materials.

SUMMARY OF THE INVENTION

An object of the invention is to provide a method for producing projection images of a specific material in a volume of the body. A further object of the invention is to provide images of a specific material with improved accuracy to enable non-invasive visualization of blood vessels. A further object of the invention is to provide a method of producing selective x-ray images which are essentially free of scattered radiation. A further object of the invention is to provide a method of producing selective x-ray images of iodinated contrast agents which are immune to the presence of intervening bone.

Briefly, in accordance with the invention, an x-ray beam is formed from an x-ray tube source which irradiates a subsection of the volume being studied. The beam is successively scanned through each subsection of the volume. At each subsection the x-ray transmission at two energy spectra is measured using integrating detectors. The resultant measurements are processed to produce a signal representing the projected amount of a specific material in the volume. The measurements are made at energy spectra where the mass attenuation coefficients of bone and soft tissue are substantially equal. A measurement at a third energy can be made to minimize the effect of intervening bone.

BRIEF DESCRIPTION OF THE DRAWINGS

For a more complete disclosure of the invention, reference may be made to the following detailed description of several illustrative embodiments thereof which is given in conjunction with the accompanying drawings, of which.

DESCRIPTION OF THE PREFERRED EMBODIMENT

Figure 1:
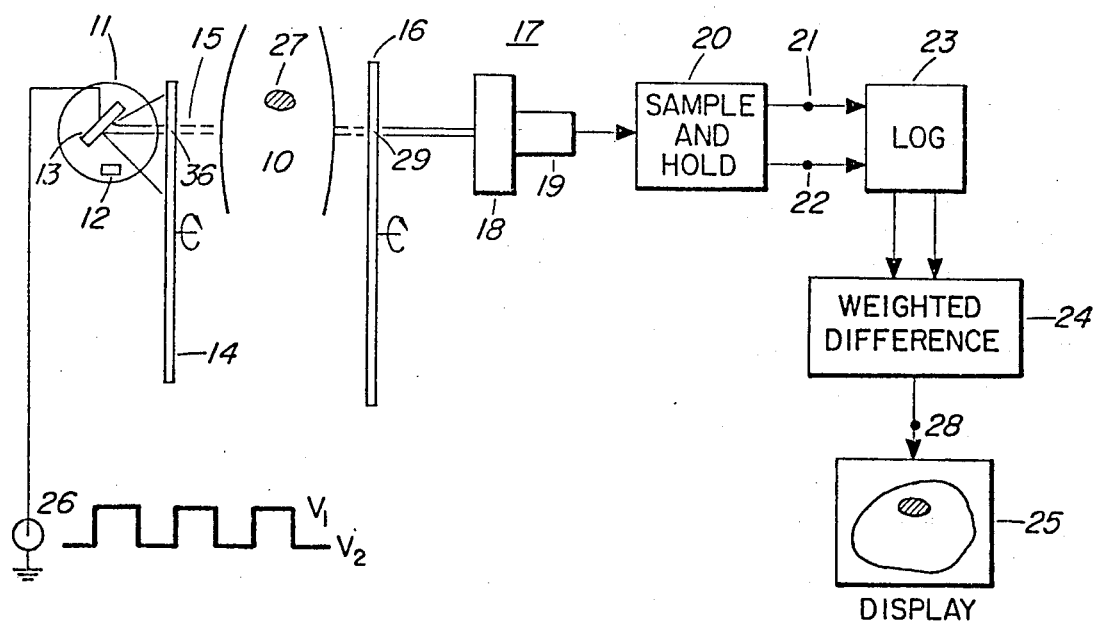
FIG. 1 is a block diagram of an embodiment of the invention using a scanning x-ray pencil beam and a changing anode voltage supply.
Figure 1A:
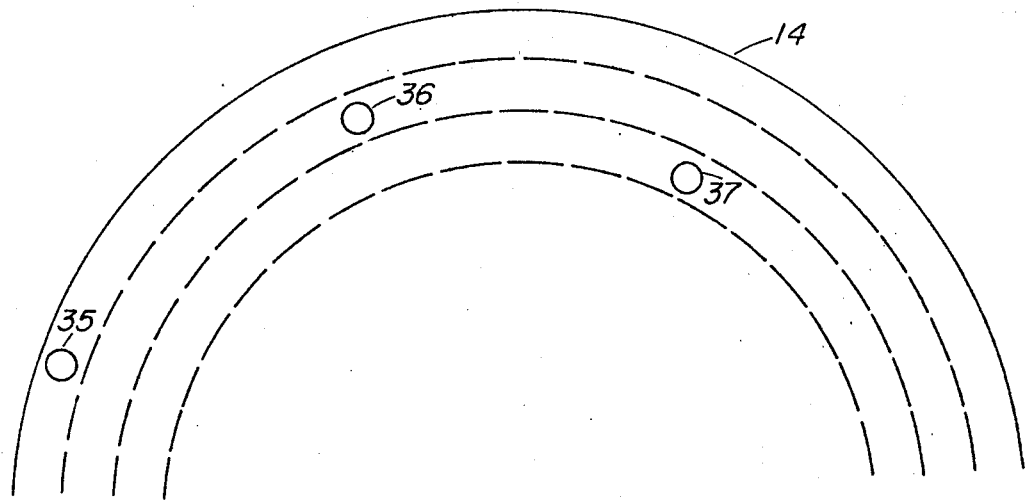
FIG. 1(a) is a schematic representation of a Nipkow disc for forming a scanning x-ray pencil beam.

An understanding of the broad aspects of the invention may best be had by reference to FIG. 1 of the drawings. A projection image 25 is made of the iodine in a volume of the subject 10. An x-ray tube source 11 is used having an anode 13 and a cathode 12. The x-ray beam emitted from anode 13 is collimated into a pencil beam 15 by aperture 36. This aperture is one of the apertures of a Nipkow disk 14, a portion of which is shown in FIG. 1(a). These disks were used in the early days of mechanical television. They represent a simple method of providing a scanned light or x-ray beam. In the case of an x-ray beam the disk must be opaque to x-rays and thus use a high absorption material such as lead. As the disk rotates, the line scan is successively provided by different apertures at different radii. Thus apertures 35, 36 and 37 each supply a single line of a total raster scan which scans the volume of interest in subject 10.

The scanned x-ray beam is applied to subject 10 having an iodinated region 27. The emerging x-ray beam, after passing through aperture 29 of a second Nipkow disc collimator 16 is applied to an integrating x-ray detector 17. This detector 17 consists of scintillating crystal 18 and photomultiplier 19. This is an integrating detector which provides an output which represents the integrated number of photons transmitted through the body. Many energy selective systems employ pulse height analyzers which measure the energy of each photon. These systems are limited to relatively slow photon rates and thus result in very long imaging times. These long imaging times are usually unsuitable for most radiographic studies. It is for the same reasons that computerized tomography systems use integrating detectors and not pulse height analyzers.

Figure 2:
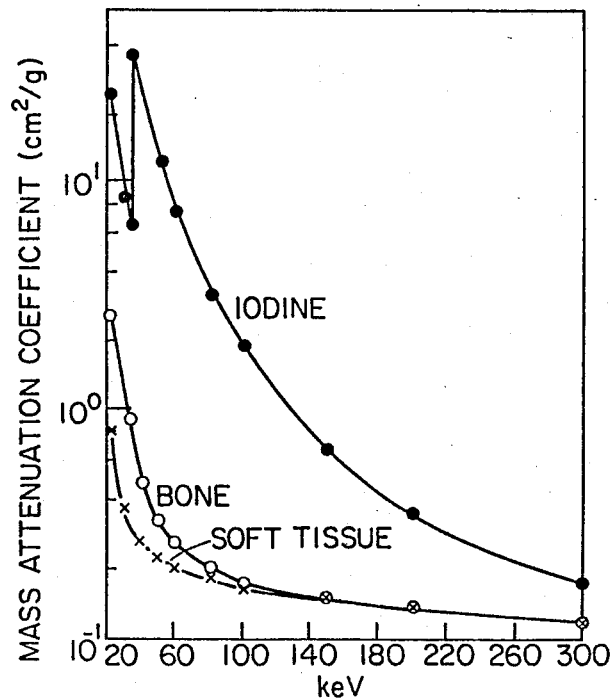
FIG. 2 is a graph indicating the mass attenuation coefficients of iodine, bone and soft tissue versus energy.

In the system of FIG. 1 the energy change is affected by changing the anode voltage 26 on anode 13 of x-ray tube 11. The anode voltage, at each position of scanning beam 15 is changed between $V_1$ and $V_2$. These voltages are chosen so as to change the effective energy of beam 15 in a manner such that the iodine content can be calculated. FIG. 2 is a graph of the mass attenuation coefficients of iodine, bone, and soft tissue as a function of energy. As is shown, above approximately 100 kev the mass attenuation coefficients of bone and soft tissue are approximately equal and slow varying. The iodine mass attenuation coefficient, on the other hand, is varying relatively rapidly. By making two measurements in the energy range where bone and soft tissue have comparable mass attenuation coefficients the iodine content can be measured. This is shown by the equations $$ln\ I_{01}/I_1 = \mu_{t1} Z_t + \mu_{I1} Z_I$$

$$ln\ I_{02}/I_2 = \mu_{t2} Z_t + \mu_{I2} Z_I$$

where $I_{01}$ and $I_{02}$ are the incident intensities at the two energies, $I_1$ and $I_2$ are the transmitted intensities, $\mu_{t1}$ and $\mu_{t2}$ are the mass attenuation coefficients of tissue at the two energies, $\mu_{I1}$ and $\mu_{I2}$ are the mass attenuation coefficients of iodine, and $Z_t$ and $Z_I$ are the equivalent path lengths of the tissue and iodine materials in gms/cm², the length multiplied by the density.

To obtain an expression proportional to the iodine content $Z_I$ a weighted difference is taken of the logs of the normalized intensities with the first equation weighted by $\mu_{t2}$ and the second by $\mu_{t1}$ giving $$Z_I(\mu_{t1}\mu_{I2} - \mu_{t2}\mu_{I1}) = \mu_{t2}\ ln\ I_{01}/I_1 - \mu_{t1}\ ln\ I_{02}/I_2$$

Thus a weighted difference of the logs of the two measurements provides a signal proportional to $Z_I$. The logs of the incident intensities $I_{01}$ and $I_{02}$ merely provide offsetting constant values.

To perform this operation a sample and hold circuit 20 is used to store the two measured outputs 21 and 22 of integrating detector 17 when the anode voltage generator 26 is changed from $V_1$ to $V_2$. Thus output 21 repesents the transmitted intensity at the average energy corresponding to anode voltage $V_2$. The lower average energy can be between 80 and 120 kev representing the energy region where bone and soft tissue have substantially equal mass attenuation coefficients as shown in FIG. 2. The higher average energy can be any value above about 120 kev where the mass attenuation coefficient of iodine has been reduced substantially below that of the lower average energy.

Logarithmic processor 23 is used to take the log of the two outputs 21 and 22. A weighted difference is taken of the logs of the measured transmitted intensities in 24 to form the processed projection signal 28 representing the projected amount of iodine in the volume of the subject 10. This signal is applied to display 25 which is raster scanned synchronously with the Nipkow disc 14. An isolated image of the iodinated region 27 is obtained.

In the prior art measurements of iodine content were made exclusively at lower energies, usually on either side of the k absorption edge. This was done to insure an adequate signal due to the large changes of $\mu_I$ in the lower energy regions. However, in this same region the attenuation coefficient of tissue $\mu_t$ is relatively high resulting in greater attenuation of the incident beam with its associated quantum noise. Thus at higher energies, the reduced iodine signal is more than compensated for by reduced quantum noise. In addition, the higher energies have an immunity to the presence of bone because of the substantial equality of the soft tissue and bone mass attenuation coefficients. Also, x-ray sources are considerably more efficient at the higher energies. These higher energies cannot profitably be used with imaging detectors because their inherent additive noise overcomes the advantage of reduced quantum noise. Thus the use of higher energies was not considered by previous investigators and they were therefore faced with difficult problems of removing the bone image from the separated iodine image.

In order to take full advantage of the fact that only a portion of the volume is being irradiated at one time the detector 17 must receive photons only from the scanning beam 15 and attenuate scattered photons. In FIG. 1 this is accomplished by a second Nipkow disk 16 which rotates synchronously with the beam forming disk 14 so that the apertures in disk 16 will always encompass the transmitted beam 15. Thus scatter from the subject 10 along the beam will be stopped by the opaque disk 16. An alternate approach not shown is the use of a scanning detector where detector 17 would have an aperture equal to the beam size and be mechanically scanned to follow the moving beam. Thus scattered photons would not be received by the detector. The wide area scintillator 18 is stationary and encompasses the imaging area. Thus it requires a moving collimator 16 for scatter elimination.

The system of FIG. 1 makes relatively inefficient use of the emitted photons from anode 13 since it uses a single pencil beam with the remainder of the emitted photons absorbed in the collimator 14. This results in relatively longer scan times and makes it difficult to study moving vessels such as the coronary arteries. This problem is reduced by the embodiment of FIG. 3 where the x-ray beam consists of an array of scanned pencil beams forming an array of contiguous rasters. In this way many more of the emitted source photons are used providing more rapid scans.

The photons emitted from anode 13 are collimated into an array of pencil beams using multiple aperture 40. One of the apertures 41 forms one of the pencil beams 15. The array of beams are projected through subject 10 and then through the second collimator 43. As in FIG. 1 this second collimator served to pass the desired array of pencil beams and attenuate the scattered radiation. For example, pencil beam 15 goes through aperture 44. Both multiple apertures 40 and 43 are synchronously scanned through small rasters using mechanical drivers 42 and 45 which provide the desired motions of the aperture plates 40 and 43. The transmitted array of pencil beams impinge on a detector system consisting of an array of scintillating crystals 46 and an array of photomultipliers 47. Each crystal photomultiplier detector element detects a small raster from one of the scanned beams.

As in FIG. 1 the anode voltage is changed with the detector outputs stored at each energy level. This could be done at two energy levels, as in FIG. 1, providing output signals 21 and 22 representing each energy level. For illustrative purposes, a three energy level system is shown where the anode voltage supply 26 is sequenced between three values; $V_1$, $V_2$ and a lower voltage $V_3$. This lower energy is used to provide a more exact correction for bone for cases where it is required. For most systems the two energies resulting from $V_1$ and $V_2$ are sufficient for providing isolated iodine images in the presence of bone and soft tissue. However, as is seen in FIG. 2, in the vincinity of 80-100 kev there remains a small difference in the attenuation coefficients of bone and soft tissue. This is particularly true if the lower energy due to anode voltage $V_2$ is reduced to about 60 kev. This might be done in some systems to provide a greater iodine signal by increasing the change in the iodine attenuation coefficient. At 60 kev the bone and soft tissue mass attenuation coefficients are different enough to cause some bone errors. This amounts to the presence of a residual bone image in the processed isolated iodine image.

Figure 3:
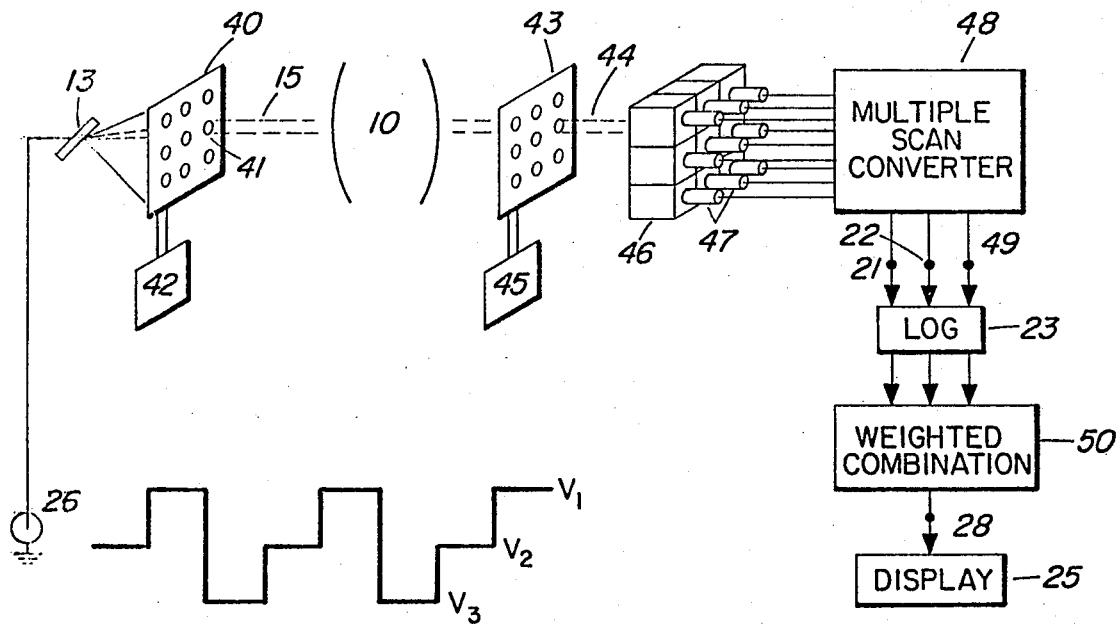
FIG. 3 is a block diagram of an embodiment of the invention using an array of scanning pencil beams and a changing anode supply providing three energy spectra.

If these bone errors are found to impair the diagnostic value of the image, they can be corrected by a third energy measurement due to anode voltage $V_3$. In FIG. 3 a multiple scan converter storage system 48 is used to store the array of detector outputs at the three energy values. These three stored projection images are then sequentially read out forming projection signals 21, 22, and 49 representing the high, medium, and low energies. The low energy due to anode voltage $V_3$ is chosen so as to have the greatest impact on the bone errors and minimize the effect on the iodine signal. A preferable energy is the region below the K edge of iodine where the iodine attenuation coefficient is reduced and the bone attenuation coefficient is relatively high. This energy region can be reached by using an appropriate anode voltage $V_3$ in the vicinity of 40-50 kv. Alternatively a small amount of iodine filtering can be used as the beam exits from the x-ray tube. This filtering will tend to concentrate the energy below the iodine K edge and it will have a negligible affect at the higher anode voltages $V_1$ and $V_2$.

To process the three signals, linear equations are again formed using the normalized logarithms of the transmitted intensities as given by $$\ln I_{01}/I_1 = \mu_{t1}Z_t + \mu_{I1}Z_I + \mu_{b1}Z_b$$

$$\ln I_{02}/I_2 = \mu_{t2}Z_t + \mu_{I2}Z_I + \mu_{b2}Z_b$$

$$\ln I_{03}/I_3 = \mu_{t3}Z_t + \mu_{I3}Z_I + \mu_{b3}Z_b$$

where $\mu_b$ is the mass attenuation coefficient of bone and $Z_b$ is the effective path length. The three equations in three unknowns can be solved for $Z_t$, $Z_I$ and $Z_b$ using standard linear algebra techniques or matrix inversion. The equation for the amount of iodine $Z_I$ will again be a weighted combination of the logs of the three measured intensities appropriately normalized. Thus the processing involves taking the logs of the intensities using logarithmic device 23 and taking weighted combinations of the logs using 50 to provide the processed projection signal 28 which is displayed in 25. In both FIG. 1 and FIG. 3 the logarithm and weighted combining would normally be done using a digital computer or using special purpose digital hardware. Analog devices can be used where less accuracy can be tolerated.

Figure 4:
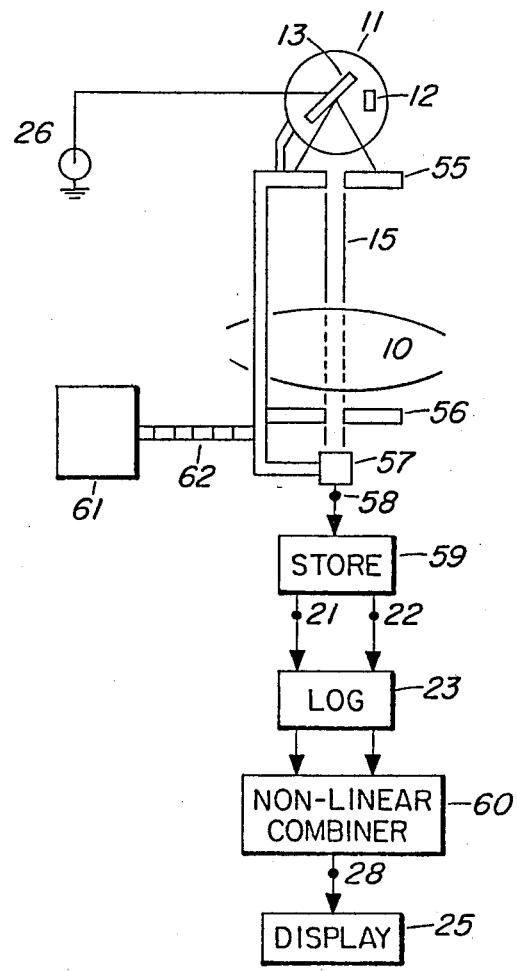
FIG. 4 is a block diagram of an embodiment of the invention using a scanning sheet beam.
Figure 4A:
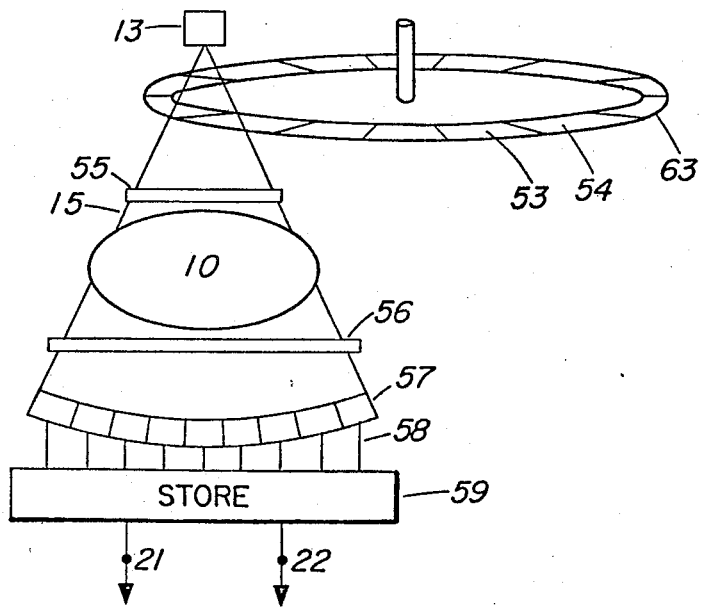
FIG. 4(a) is a schematic representation of an embodiment using a sheet beam and a filter wheel for changing energy.

The mechanical motions of FIG. 3 can be relatively complex. A more straightforward multiple detector system is shown in FIGS. 4 and 4(a). Here the x-ray output from anode 13 is collimated into a fan shaped sheet beam 15. This configuration is similar to that used in the General Electric Scout View system of projection radiography using a computed tomography instrument. FIGS. 4 and 4(a) represent two views of the configuration. The x-ray output from anode 13 of x-ray tube 11 is collimated into a fan-shaped sheet beam 15 using collimator 55. This collimator consists of an opaque region with a slit opening forming the sheet beam 15. The beam is projected through subject 10 and again collimated using a second collimator 56. This second collimator 56 allows sheet beam 15 to pass and it attenuates scattered radiation from the subject 10. The beam is then detected by detector array 57 which provides an array of measurement signals 58 along the fan-shaped sheet beam.

In the configuration shown the entire system, x-ray tube 11, collimators 55 and 56 and detector 57 are mechanically connected together and scanned in a director normal to the plane of the sheet beam 15. This provides a projection image of a volume of the subject 10. The structure can be scanned using motor drive 61 and lead screw 62 to index sheet beam 15 along subject 10. Subject 10 remains stationary. In an alternative configurations, not shown, detector array 57 can consist of an array of elongated detector elements which span the entire image. In this alternate configuration detector 57 is not scanned but remains stationary as the collimated sheet beam 15 is scanned along the elongated elements. In this alternate configuration the second collimator 56 is particularly important in eliminating scatter since the elongated detector can receive scatter from the entire volume. Collimator 56 is less important in the configuration shown where the detector consists of a single scanned line and is relatively immune to scatter. Another, less desirable, mode of operation is to leave the beam 15 and detector 57 fixed and scan the patient 10. This is adequate for studies of relatively static organs but not for rapidly moving organs.

The energy modulation can take place exactly as indicated in FIG. 1. Anode supply 26 is indexed between two voltages. Or, the anode to cathode voltage can vary sinusoidally. One method of X-ray tube control is to utilize a tube with a control grid, and pulse the grid at times corresponding to different anode to cathode voltages. Storage system 59 stores the array of measurement signals 58 at each of the two energies to provide measurement signals 21 and 22 representing the high and low energy transmission. These can be processed exactly as in FIG. 1 to provide the projection signal 28 representing the specific material in the volume of interest.

In the system of FIG. 1, however, the processing system operates under the assumption that the high and low energy spectra can be approximated by monoenergetic spectra at the average energies. This has been found to be a good approximation, especially in the higher energy regions where $\mu$ is a slow function of energy. However, to be more accurate, the beam hardening affects can be taken into account. In that case the line intergrals, $\mu z$, are nonlinear functions of the log of the transmitted intensities. FIG. 4 shows a method of more accurate processing using nonlinear combiner 60 where weighted sums and differences are taken of nonlinear combinations of the log of the measurement signals. For example, a weighted difference can be taken of both the logs of measurement signals 21 and 22, as was done in FIG. 1, and an additional weighted difference can be included of the squares of the differences of logs of these signals. These squared components will be relatively small compared to the original components since the beam-hardening effect is small. In more complex nonlinear processing, higher order terms can be used including terms combining both measurement signals. These corrections, in general, are similar to the nonlinear beam-hardening corrections used in all commercial CT scanners.

FIG. 4(a) shows an alternate configuration for changing the energy of the beam 15. Instead of changing the anode voltage, the energy is changed by inserting a sequence of filters in the path of the x-ray beam. Rotating filter wheel 63 has an array of x-ray filters in the form of an annulus. These filters are sequenced in front of anode 13 to successively change the beam energy spectrum. For example, in a system using two energies, the filter wheel 63 would consist of alternating filters 53 and 54. Filter 53 can be the lower energy filter, such as tungsten, which has K edge at about 70 kev. Thus the energy spectrum would peak somewhat below 70 kev. Filter 54 can be the higher energy filter, such as uranium, which has a K edge at 115 kev. The K edge phenomenon need not be used for the filtering. Relatively lower atomic number materials can be used which eliminate the lower energies and thus increase the mean energy of the beam. Combinations of anode voltage changes and filter changes can be used to provide greater flexibility of the chosen energy spectra. For a system using three energies, as in FIG. 3, the filter wheel 63 would consist of three repetitive filter segments. The third segment could be iodine to create the desired mean energy below the iodine K edge for bone correction. The filter changes can be used with any of the previously described scanning systems such as those of FIGS. 1 and 3. As with the high voltage changes, storage system 58 stores the outputs at each energy spectrum forming measurement signals 21 and 22.

Figure 5:
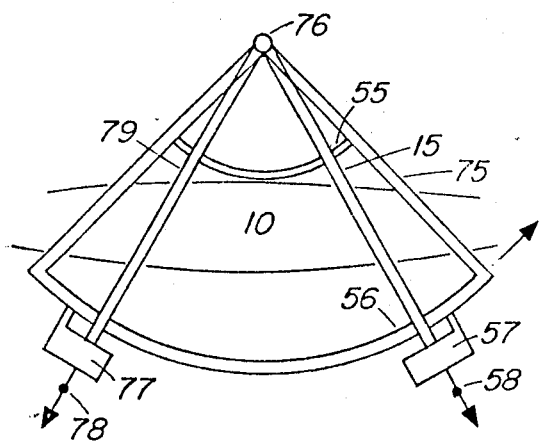
FIG. 5 is a schematic representation of an embodiment of the invention using oscillated multiple sheet beams.

Often rapid repetitive scanning is desired for resolving motion. The configuration of FIG. 4 might be somewhat limited in its ability to provide a sequence of repeated rapid scans in the order of ten per second. The oscillating configuration of FIG. 5 is more suited to provide rapid repetitive scans. The x-ray tube source, not shown, remains stationary in the vicinity of the pivotal bearing 76. Ignoring detector 77 and its associated collimators, structure 75 contains source collimator 55, second collimator 56 and detector 57. This entire structure is rotated back and forth around pivot 76 to provide a sheet beam 15 which successively sweeps through the desired volume of subject 10. Signals 58 are processed exactly as previously described to provide the processed projection image signal. The energy of beam 15 can be changed in any of the previously described manners.

To provide more rapid studies it is desirable to both increase the collection efficiency of the emitted x-ray photons and to minimize the amount of mechanical movement required. This is shown in FIG. 5 where additional sheet beams and detectors are used to simultaneously collect measurement signals from a number of slices. For simplicity a single additional sheet beam 79 is shown in FIG. 5. This is formed using an additional aperture in source collimator 55 and in the second collimator 56. The transmitted photons for the second sheet beam 79 are collected in detector 77 to provide an array of detector output signals 78. Both the energy change mechanisms and the signal processing mechanisms for the system of FIG. 5 can be any of those previously described. Using multiple sheet beams, the structure 75 is oscillated over a smaller angle since each sheet beam scans a portion of the volume. Thus the scan time is decreased due to the smaller scanning volume for each sheet beam.

Figure 6:
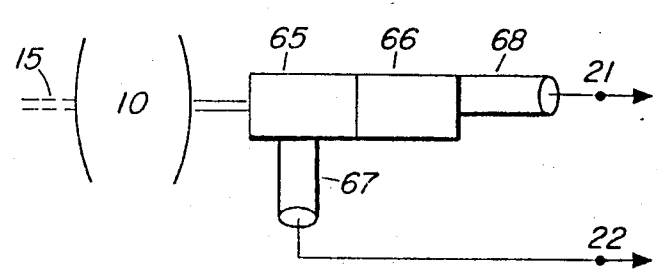
FIG. 6 is a schematic representation of an embodiment of the invention using an energy-sensitive detector.

In the embodiments previously described measurements at different energy spectra were obtained by sequentially changing the energy of the x-ray beam. An alternate approach is shown in FIG. 6 where the two measurements are obtained simultaneously, thus reducing the scanning time. In FIG. 6 the beam 15, after passing through the subject 10, is detected using an energy sensitive integrating detector. This is in sharp distinction to energy sensitive detectors using pulse-height analysis. These latter detectors require the isolation of single photon events and are thus limited to relatively low values of x-ray intensities. These reduced intensities result in very long exposure intervals which are unsuitable for dynamic organs.

Integrating energy-sensitive detectors, as previously indicated, are described in U.S. Pat. No. 4,029,963. As shown in FIG. 6, beam 15 goes through two scintillating materials, 65 and 66. These can both be the same material, such as sodium iodide, or they can have different materials. In general the lower energy photons will give up their energy in the first portion 65 since these photons have a smaller mean free path. The higher energy photons with a longer mean free path will tend to give up their energy in the second scintillator 66.

Photomultiplier 67 receives the light from the first scintillator 65 to provide the lower energy measurement 22. Photomultiplier 68 receives the light from the second scintillator 66 to form the higher energy measurement 21. These measurement signals at the two energies, 21 and 22, are processed exactly as shown in FIG. 2 to provide the desired processed signal 28. Alternatively they can be processed as in FIG. 4 to correct for the nonlinearities. A thin separator which is opaque to light and passes x-rays can be placed between scintillator 65 and 66 to minimize cross talk.

Although FIG. 6 shows a single channel, an array of dual detectors can be used in the configuration of FIG. 4. In that case anode voltage changes are not required since arrays of measurements at each energy will be simultaneously available. In addition to scintillation detectors, ionization detectors using gases such as Xenon can be used. A split pickup electrode can be used with the front half receiving primarily lower-energy photons and the back half receiving primarily higher energy photons as described in the previously referenced U.S. Pat. No. 4,029,963.

The energy sensitive detector of FIG. 6 can also be used with the three-energy spectra system introduced in FIG. 3 where a lower energy measurement is used to aid in the removal of bone artifacts. An additional scintillator not shown, can be added on the x-ray beam side to receive the lower energy photons. It would be preferable if the materials used produced scintillations primarily below the iodine K edge so as to provide a measurement spectrum in that region. This third signal is used exactly as previously described in connection with FIG. 3. Also, the desired spectral measurements can be achieved through a combination of energy changes of the beam and energy sensitive detection.

Figure 7:
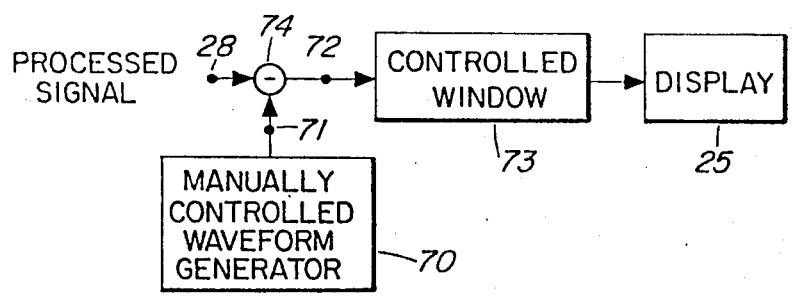
FIG. 7 is a block diagram of an arrangement for controlled contrast enhancement.

Systems of computerized tomography achieve high contrast displays through the use of controlled windowing. The operator can control both the center value and the range of the displayed values so that subtle changes produce high contrast in the display. As shown in FIG. 7 a controlled windowing system 73 can also be used with this selective projection imaging system to provide a high contrast display. Processed signal 28 is appropriately amplified and clipped at the desired level before being displayed on display 25. This can aid, for example, in the visualization of coronary arteries.

In some cases, when an isolated iodine image 28 is formed, there exists an undesired iodinated background such as the heart chambers in the path of the coronary arteries. This background can be minimized by having the operator subtract portions of it before the windowing operation. The operator can manually adjust waveform generator 70 to eliminate the background from various selected regions of the coronary arteries while observing the display 25. Generator 70 produces signal 71 which is subtracted from the processed signal 28 in subtractor 74 to produce corrected signal 72. The subtractor can be a simple difference amplifier. Alternatively an automatic system can be used with a line following algorithm which follows the coronary artery and generates the required subtraction signal 71 at each point. Line-following algorithms have been widely published in the image processing literature.

Figure 8:
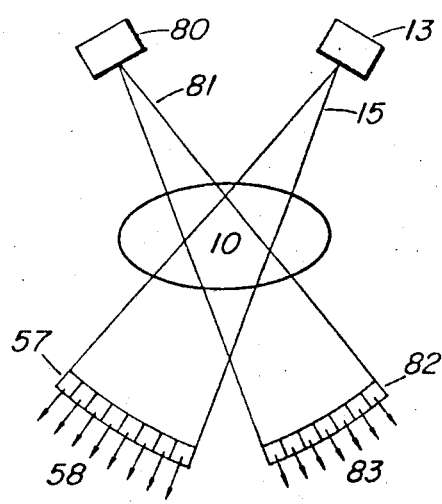
FIG. 8 is a schematic representation of an embodiment of the invention employing two views.

In the systems described a single projection image of a selective material in a volume of the body was produced. In many diagnostic procedures, however, it is desirable to provide two views to help to define the anatomy in three dimensions. This can be accomplished using the system of FIG. 8 where two fan beam systems, of the type shown in FIG. 4, are simultaneously used to collect line projections. X-ray sources 13 and 80 produce sheet beams 15 and 81 with collimators not shown.

These beams are projected through subject 10 and detected using line arrays 57 and 82 to provide measurement arrays 58 and 83. Any of the previously described energy sensitive systems can be used including sequential changing of the source of energy-sensitive detection. The measurements 58 and 83 are processed as previously described to produce two displays which represent the two views and help to identify the anatomy in space. Stereo viewers can be used by the operator.

The two fan beams and their detectors are simultaneously translated with respect to subject 10 to provide the projection images. For convenience it may be desirable if each beam intercepts a different plane in object 10 to avoid difficulties with the hardware. In the two displays, however, each line would be at the same level. For economy reasons a single beam can be used to acquire the two views in sequence. This can, however, produce severe motion artifacts.

Although iodinated contrast agents were used as examples, many other administered and natural body materials can be isolated using this system For example in chest radiography it is often desirable to visualize lesions, such as tumors, which underlie or overlie bone structures. If the system is used to separate bone and soft tissue, and thus provide separate images of each, this problem can be solved. Using lower energy measurements where bone and soft tissue have different attenuation coefficients a soft tissue only image can be formed to eliminate the bone and allow the visualization of the lesions.

Systems of this type require considerable accuracy in the measurements. It is therefore desirable to carefully monitor the source intensity for considerations of drift. An additional reference detector, as is used in CT systems, can be used to monitor the x-ray output is a region outside of the transmitted beam. A length of tissue-equivalent material can be used between the source and the reference detector to provide a standardized reference to aid in the calculations. Since it is known that the material contains no iodine, it can facilitate compensating for a variety of errors in the system by requiring that the processor indicate zero iodine content for the reference signal.

A variety of mechanical scanning systems have been shown for providing scanned x-ray beams having different configurations. These mechanical systems can be eliminated by using electronically scanned electron beams. These scanned electron beams, in special purpose x-ray tubes, can be scanned over anodes to provide an electronically movable x-ray source. This moving source, in connection with fixed collimators, provides a scanned x-ray beam without mechanical motion.

In the system using changing anode voltage, the anode voltage was stepped from one value to the next, as shown in FIGS. 1 and 3. This can be difficult to achieve if it is done rapidly. Since the mean energy is the important parameter being changed, it is not essential for the anode voltage to remain constant during the photon collection interval. For example, sinusoidal anode voltages can be used with the data for the higher energy collected during the positive half cycle and that for the lower energy collected during the negative half cycle. These sinusoidal anode voltages are much easier to generate. Another alternative involves grid control within the x-ray tube. A varying anode voltage can be used with the grid-controlled x-ray tube turned on during the desired voltage ranges. For example, using a sinusoidal anode voltage, the x-ray tube can be switched on during the region of the maximum and minimum values and turned off during the transition regions of the sine wave.

The temporal requirements for this system are different from conventional x-ray imaging systems using imaging detectors such as film or television fluoroscopy. With imaging detectors, when viewing moving structures such as the coronary arteries, it is essential that the exposure take place during a time interval of under 50 milliseconds where the structures are relatively stationary. In the systems described in this application each subsection of the volume is exposed in sequence. This results in a "focal-plane shutter" effect where each region is exposed at a different time. In this case it is essential that each subsection exposure take place during a time interval where the structures of interest are relatively stationary. The entire exposure, however, can take place over a time interval long as compared to the motion, as with the focal-plane shutter. The resultant image will not be blurred or smeared due to the motion since the structure is essentially stationary during each subsection exposure. The image will, however, be distorted in that different portions of the anatomy will be viewed at different times. For example, a vertical vessel moving horizontally will result in an image of a somewhat tilted vessel since each line will be exposed at a slightly different time. The diagnostic value of this skewed image of the vessel is not impaired since narrowing or stenosis of the vessel can be observed with good clarity since no blurring or smearing has taken place. If an imaging detector were used with a long exposure interval the image of the moving vessel would be significantly blurred by the motion, thus greatly reducing its diagnostic value. Using the configuration of FIG. 4 typical exposure times would be 1–10 milliseconds per line resulting in 0.2–5 seconds per total image. The short line exposure interval makes it excellent for cardiovascular visualization despite the long image time.

In this system only a subsection of the volume is irradiated at one time greatly reducing scatter and allowing the use of efficient non-imaging detectors. These detectors have negligible additive noise thus greatly increasing the sensitivity of the measurements. The unique combination of this x-ray imaging system with multiple-energy measurements allows the imaging of small amounts of specific materials. These detectors also facilitate the use of higher energies with their improved quantum statistics and immunity to bone. These properties are unique in that they allow the non-invasive imaging of small vessels such as the coronary arteries.

What is claimed is:

1. In a method for producing a low-scatter two-dimensional projection image of a specific material within a volume of the body the steps of:
   forming an x-ray beam from the x-rays emitted from an x-ray source which irradiates a subsection of the volume and a corresponding subsection of the two-dimensional projection image;
   collimating the x-ray beam emerging from the volume;
   measuring the x-ray transmission through each subsection of the volume at two energy spectra using an integrating detector which receives transmitted x-rays substantially only from the extent of the collimated x-ray beam whereby most scattered radiation is eliminated;
   synchronously scanning the x-ray beam and integrating detector with respect to the volume over the entire two-dimensional projection image;
   processing the measurements at the two energy spectra to produce a processed two-dimensional projection signal representing the projected amount of the specific material in the volume; and
   displaying the processed projection signal to provide a two-dimensional projection image of the specific material in the volume.

2. The method as in claim 1 wherein the step of measuring the x-ray transmission at two energy spectra includes the step of varying the energy of the scanning x-ray beam at each subsection.

3. The method as in claim 1 wherein the step of measuring the x-ray transmission at two energy spectra includes the step of detecting the transmitted x-rays using an energy-sensitive detector.

4. The method as in claim 1 where the material being imaged is iodine and the step of measuring the x-ray transmission of the volume at two energy spectra includes the step of measuring the x-ray transmission at a first energy at which the mass attenuation coefficients of bone and soft tissue are substantially equal and the step of measuring the x-ray transmission at a second energy at which the mass attenuation coefficients of bone and soft tissue are substantially equal and the mass attenuation coefficient of iodine is substantially different than that of the first measurement.

5. The method as in claim 1 including the step of measuring the x-ray transmission of each subsection of the body at a third energy spectra and the step of processing this measurement along with those of the two energy spectra to remove the effects of bone.

6. The method as in claim 5 where two of the energy spectra are above the iodine K edge energy and the third energy spectra is below the iodine K edge energy.

7. In a method for providing low-scatter multiple energy two-dimensional x-ray transmission measurements of a volume the steps of:
   collimating the emitted beam from the x-ray source into a planar fan beam;
   scanning the fan beam through the volume in a direction normal to the plane of the fan beam;
   collimating the fan beam emerging from the volume;
   synchronously scanning a detector array which substantially intercepts only the collimated planar fan beam emerging from the volume whereby most of the scattered radiation is eliminated; and
   measuring the x-ray transmission at each position of the scanning planar beam at two energy spectra using the detector array.

8. In a method for providing low-scatter two-dimensional projection images of a specific material in regions of the body containing moving structures the steps of:
   collimating the emitted beam from an x-ray source into a planar fan beam which spans a subsection of the body;
   scanning the fan beam through the volume in a direction normal to the plane of the fan beam at a speed such that the time spent at each subsection involves substantially no motion of the moving structures;
   collimating the fan beam emerging from the volume;
   synchronously scanning a detector array which substantially intercepts only the extent of the collimated planar fan beam emerging from the volume whereby most scattered radiation is eliminated;

measuring the x-ray transmission at each position of the scanning beam at two energy spectra;

processing the measurements to provide a processed two-dimensional projection signal representing the projected amount of the specific material in the volume; and displaying the processed two-dimensional projection signal to provide a two-dimensional image of the specific material in the volume.

9. In a method for providing isolated two-dimensional projection images of bone and soft tissue within a volume the steps of:

collimating the emitted beam from an x-ray source into a planar fan beam;

scanning the fan beam through the volume in a direction substantially normal to the plane of the fan beam;

collimating the fan beam emerging from the volume;

synchronously scanning a detector array which substantially intercepts only the extent of the collimated planar fan beam emerging from the volume whereby most scattered radiation is eliminated;

measuring the x-ray transmission, using the detector array, at two energy spectra where the relative mass attenuation coefficient of bone and soft tissue are substantially different at each spectra;

processing the measurements to provide two-dimensional projection signals representing the projected amounts of bone and soft tissue; and displaying one of the processed projection signals.

10. Apparatus for providing a two-dimensional projection image of a specific material within a volume of the body comprising:

an x-ray tube source producing x-rays which are collimated into an x-ray beam which is projected through a subsection of the volume onto a subsection of the two-dimensional image;

collimation means for receiving and collimating the x-ray beam emerging from the volume, means for sequentially scanning the collimated x-ray beam with respect to the volume through each subsection of the volume and the two-dimensional image;

means for measuring the transmission of the x-ray beam through the volume at two energy spectra using an integrating detector which intercepts substantially only the extent of the x-ray beam whereby most scatter is eliminated;

means for processing the transmission measurements to produce a processed projection signal representing the projected amount of the specific material in the volume; and means for displaying the processed projection signal to produce a two-dimensional projection image of the specific material.

11. Apparatus as recited in claim 10 wherein the means for measuring the transmission of the x-ray beam through the volume at two energy spectra includes means for sequentially changing the energy spectrum of the x-ray tube source.

12. Apparatus as recited in claim 11 wherein the means for sequentially changing the energy spectrum of the x-ray tube source includes changing the anode to cathode voltage of the x-ray tube.

13. Apparatus as recited in claim 12 wherein the means for changing the anode to cathode voltage of the x-ray tube includes the application of a sinusoidally varying voltage component between the anode and the cathode of the x-ray tube.

14. Apparatus as recited in claim 12 wherein the x-ray tube has a control grid and the means for changing the anode to cathode voltage of the x-ray tube includes applying a time varying voltage between anode and cathode and pulsing the control grid at times corresponding to different anode to cathode voltages.

15. Apparatus as recited in claim 11 wherein the means for sequentially changing the energy of the x-ray tube source includes means for sequentially inserting x-ray filter material in front of the x-ray tube source.

16. Apparatus as recited in claim 10 where the integrating detector is energy sensitive and the means for measuring the transmission of the x-ray beam through the volume at two energy spectra includes means for providing separate detector outputs at the two energy spectra.

17. Apparatus as recited in claim 16 wherein the energy sensitive detector comprises two sections including a first section receiving the x-ray beam after it leaves the volume and a second section receiving the x-ray beam after it passes through the first section and including means for measuring the absorbed energy in each section.

18. Apparatus as recited in claims 10, 11, or 16 wherein the x-ray beam is a pencil beam, the subsection of the volume is the projection of the pencil beam and the scanning means includes means for moving the pencil beam through a two-dimensional raster scan.

19. Apparatus as recited in claim 18 including a scanning aperture moving synchronously with the scanned pencil beam and positioned between the volume and the means for measuring the transmission of the x-ray beam whereby scattered x-rays are further prevented from being detected.

20. Apparatus as recited in claims 10, 11, or 16 wherein the x-ray beam is an array of pencil beams, the subsection of the volume is the sum of the projections of the array of pencil beams and the scanning means includes means for moving the array of pencil beams through individual raster scans which combine to scan the entire volume.

21. Apparatus as recited in claim 20 including a multiple scanning aperture moving synchronously with the array of pencil beams and positioned between the volume and the means for measuring the transmission of the x-ray beam whereby scattered x-rays are further prevented from being detected.

22. Apparatus as recited in claim 20 where the integrating detector includes an array of detectors each detecting one of the array of pencil beams.

23. Apparatus as recited in claims 10,11,12,13,14,15,16 or 17 where the x-ray beam is a sheet beam, the subsection of the volume is a thin planar section and the scanning means includes means for translating the sheet beam in a direction substantially normal to the plane of the beam.

24. Apparatus as recited in claim 23 where the integrating detector is a linear detector array positioned to detect the transmitted sheet beam and produce an array of measurements representing the transmission of the sheet beam through the volume at two energy spectra.

25. Apparatus as recited in claim 24 including a sheet beam collimator positioned between the linear detector array and the volume which allows passage of the transmitted sheet beam to the linear detector array and further prevents scattered radiation from reaching the detector array.

26. Apparatus as recited in claim 23 including a slit collimator between the x-ray source and the volume for producing the sheet beam and where the scanning means includes means for moving the slit collimator with respect to the x-ray source in a direction normal to the slit.

27. Apparatus as recited in claim 26 where the scanning means further includes means for sequentially oscillating the slit collimator in a direction normal to the slit whereby a sequence of projection images are provided for dynamic studies.

28. Apparatus as recited in claims 10,11,12,13,14,15,16 or 17 wherein the x-ray beam is a plurality of sheet beams and where the integrating detector is a plurality of linear detector arrays with each detector array detecting the transmitted radiation from each sheet beam.

29. Apparatus as recited in claim 28 including a plurality of sheet beam collimators positioned between the linear detector array and the volume which allows passage of each of the plurality of sheet beams and further prevents scattered radiation from reaching each of the linear detector arrays.

30. Apparatus as recited in claims 10, 11, or 16 further comprising:
a second x-ray source producing a second x-ray beam which is projected through a subsection of the volume of the body at a second angle different than that of the first x-ray source;
means for sequentially scanning the second x-ray beam through each subsection of the volume;
means for measuring the transmission of the second x-ray beam through the volume at the same two energy spectra as that of the first x-ray beam;
means for processing the transmission measurements to produce a second processed projection signal representing the projected amount of the specific material in the volume at the second angle; and
means for displaying the second processed projection signal.

31. Apparatus as recited in claims 10, 11, or 16 where the volume of the body contains bone and soft tissue, the specific material is an iodinated contrast agent and the two energy spectra used for measuring the transmission through the body are in regions such that the mass attenuation coefficients of bone and soft tissue are substantially equal to each other at each energy spectrum and the mass attenuation coefficients of iodine are substantially different at each energy spectrum whereby the iodine information can be separated with two measurements.

32. Apparatus as recited in claims 10, 11, 12, 13, 14, 15, 16 or 17 including means for measuring the transmission of the x-ray beam through the volume at a third energy spectrum whereby the specific material can be separated from two types of tissue within the volume of the body.

33. Apparatus as recited in claim 32 where the volume of the body contains bone and soft tissue, the specific material is an iodinated contrast material and the third energy spectrum has a mean energy below the K edge of iodine.

34. Apparatus as recited in claim 10 wherein the time required to scan through each subsection of the volume is sufficiently small that moving structures in the volume of the body are essentially stationary.

35. Apparatus as recited in claim 10 including means for subtracting portions of the two-dimensional processed projection signal and windowing the resultant signal prior to the display whereby vessel images may be separated from background structures.

36. Apparatus as in claims 10, 11 or 16 wherein the means for processing the transmission measurements includes means for combining nonlinear functions of the logarithms of the measurements whereby the beam hardening of each measurement is corrected.

37. Apparatus as recited in claims 10,11,12,13,14,15,16 or 17 wherein the specific materials are bone and soft tissue and the two energy spectra are chosen such that the relative values of the mass attenuation coefficients of bone and soft tissue are substantially different in each of the two energy spectra.

38. Apparatus for providing a projection image of a specific material within a volume of the body containing bone and soft tissue comprising:
an x-ray source producing an x-ray beam which is projected through the volume;
means for measuring the transmission of the x-ray beam through the volume at a first energy spectra where the mass attenuation coefficients of bone and soft tissue are substantially equal;
means for measuring the transmission of the x-ray beam through the volume at a second energy spectra where the mass attenuation coefficients of bone and soft tissue are substantially equal and the mass attenuation coefficient of the specific material is substantially different than its value at the first energy spectra; and
means for processing the measurements to provide a projection image of the specific material.

39. Apparatus as recited in claim 38 wherein the means for measuring the transmission of the x-ray beam through the volume at the two energy spectra includes means for sequentially changing the energy spectrum of the x-ray beam and detecting the transmitted x-ray beam.

40. Apparatus as recited in claim 38 wherein the means for measuring the transmission of the x-ray beam through the volume at the two energy spectra includes an energy sensitive detector providing individual measurements at each energy spectra.

41. In a method for providing a projection image of a specific material within a volume of the body containing bone and soft tissue the steps of:
measuring the x-ray transmission of the volume at a first energy spectra where the mass attenuation coefficients of bone and soft tissue are substantially equal;
measuring the x-ray transmission of the volume at a second energy spectra where the mass attenuation coefficients of bone and soft tissue are substantially equal and the mass attenuation coefficient of the specific material is substantially different than its value at the first energy spectra; and
processing the measurements to produce a projection image of the specific material in the volume.

* * * * *